United States Patent [19]

Anderson et al.

[11] Patent Number: 4,550,187

[45] Date of Patent: Oct. 29, 1985

[54] SYNTHESIS OF PLATINUM (IV) ANTINEOPLASTIC AGENTS

[75] Inventors: Wayne K. Anderson, Williamsville; Dominick A. Quagliato, Amherst, both of N.Y.

[73] Assignee: The Research Foundation of State University of New York, Albany, N.Y.

[21] Appl. No.: 599,642

[22] Filed: Apr. 12, 1984

[51] Int. Cl.$^4$ .............................................. C07F 15/00
[52] U.S. Cl. ................................................... 556/137
[58] Field of Search .................................... 260/429 R

[56] References Cited

U.S. PATENT DOCUMENTS 4,431,666  2/1984  Bulten et al. .............. 260/429 R X
4,466,924  8/1984  Verbuk et al. .................. 260/429 R
4,482,569  11/1984 Bulten et al. .............. 260/429 R X Primary Examiner—Helen M. S. Sneed
Attorney, Agent, or Firm—Omri M. Behr

[57]  ABSTRACT

There is provided a method of synthesizing tetrachlorocyclohexanediammine platinum (IV) compounds in high purity and yield, the level of purity being suitable for pharmacological use. The compounds produced by this process have antineoplastic agents against tumor cells resistant to cis-platinum.

5 Claims, No Drawings

SYNTHESIS OF PLATINUM (IV) ANTINEOPLASTIC AGENTS

BACKGROUND OF THE INVENTION

Cis-platinum is currently used as a clinically effective antineoplastic agent. However, in view of inherent problems of toxicity, poor stability and resistance of certain tumors to the drug, new platinum based antineoplastics have been sought. Among the work which is of interest in this area are derivatives of 1,2-diaminocyclohexane platinum (II) SHP, which have been reported by Hall, et al., (Wadley Medical Bulletin, 7, 231–241 (1977)). Among the compounds reported by the Wadley group as being of very modest activity are the tetrachloro platinum derivatives of 1,2-diaminocyclohexane. The Wadley work discloses no synthetic route and no chemical characterization or levels of purity. At substantially the same time, a very brief report of a synthetic route to this compound was disclosed by Schwartz, et al., (Cancer Treat. Rep., 61, 1519 (1977)). This report discloses an 80% yield and, based upon platinum percentage, a fairly good level of purity. Nevertheless, no physical data is supplied by the Schwartz paper.

The oxidation of dichloro (bis ethylene diamine) Pt (II) to the corresponding tetrachloro Pt (IV) is reported by Basolo, et al., (JACS, 72, 2433–2436 (1950)) who carry out the reaction in water.

In view of renewed interest in the platinum (IV) compounds by other workers, new synthetic routes were sought to provide tetrachloro-1,2-diaminocyclohexane platinum (IV) (abbreviated, hereinafter as tetrachloro DACH Pt (IV) in good yields and high levels of purity.

SUMMARY OF THE INVENTION

The process of synthesis of the tetrachloro DACH Pt compounds comprises two novel steps of synthesis and one novel isolation step. The dichloro DACH Pt (II) is prepared by reacting 1,2-diaminocyclohexane with alkali metal chlorplatinate in degassed water in an inert atmosphere. The purpose of this procedure is to remove the carbon dioxide which complexes with 1,2-diaminocyclohexane and reduces the yield of the reaction. The oxidation step to the tetrachloro compound in contrast to the prior art procedure (Schwartz) which utilizes hydrogen peroxide and hydrochloric acid in water is carried out with chlorine in hydrochloric acid (again in contrast to the procedure of Basolo who utilizes water as the medium). The unreacted chlorine is removed from the reaction mixture by air purging and the product purified. The novel and unsuggested mode of purification comprises solution in a lower alkanol, suitably methanol, to remove insolubles and recrystallization from aqueous hydrochloric acid. The process of the present invention has been carried out starting with the appropriate 1,2-diaminocyclohexane to produce all possible stereochemical variations of tetrachloro DACH Pt (IV), namely the cis, the d,1-trans, the 1R,2R-trans and the 1S,2S-trans. The tetrachloro DACH platinum (IV) compounds prepared by the process of the present invention have been shown to be active against cisplatin resistant L1210 lymphocytic leukemias.

DESCRIPTION OF THE PREFERRED EMBODIMENTS

The starting materials for the process of the present invention are stereochemically characterized 1,2-diaminocyclohexanes, namely the cis, the racemic trans and the two resolved trans forms.

The separation of cis and the trans forms is carried out by the method of Kibani and Saito, (Chem. Lett., (1976), 123.) In this procedure a solution of 1,2-diaminocyclohexanes in methanol is added to a similar solution of nickel dichloride to provide after some period of time, a yellow-green solid precipitate of the cis complex and a violet filtrate of the d1-trans recemate complex. The filtrate is caused to precipitate by adjustment of the pH to between 4.2 and 4.5. Both nickel complexes are appropriately separated.

The nickel complexes are decomposed with strong aqueous sulfuric acid to provide the corresponding diaminocyclohexane hydrosulfate which, after isolation, is in turn decomposed with aqueous alkali and the product extracted in a suitable organic solvent such as benzene.

Where it is desired to further resolve the racemic trans mixture, in place of the sulfuric acid, there is utilized either d- or 1- tartaric acid and the resultant product resolved by differential crystallization in the usual manner prior to alkaline decomposition.

The diamonicyclohexane is converted into the corresponding dichloro-1,2-cyclohexanediamine platinum (II) by reaction with potassium tetrachlorplatinate (II). (Kidani, et. al., J. Med. Chem., 21, 1315 (1978)). In this improved process the DACH is taken up in water previously degassed by vacuum purging and added to a stirred solution of potassium tetrachlorplatinate (II) in similarly degassed water. Equimolar amounts are used, the reaction is carried out in an inert atmosphere suitably under a nitrogen blanket, and the mixture stirred at ambient temperature for from about 12 to about 24, suitably for about 18 hours. A pale yellow precipitate is provided which is further purified by solution in a polar nitrogenous solvent such as dimethylformamide and precipitated therefrom with a lower alkanol suitably by methanol. The oxidation to the tetrachloro DACH platinum (IV) is carried out in dilute hydrochloric acid by the action of chlorine gas. The dichloro DACH Pt (II) is suspended in dilute hydrochloric acid, suitably between about 0.1 and 2N, preferably between 0.2 and 0.75N, warmed to between 40°–80° and chlorine gas bubbled under the surface of the suspension. An immediate color change to redorange is noted, changing to bright yellow with partial dissolution. It is desirable to raise the temperature of the reaction mixture during the chlorine addition to approximately 100° C. After completion of the chlorine addition, the unreacted chlorine is removed by air purging, the reaction mixture cooled and evaporated by dryness in vacuo to provide the impure tetrachloro DACH Pt (IV). The product is taken up in methanol, filtered to remove insolubles, and evaporated to dryness to yield the desired product, which may then be recrystallized from dilute hydrochloric acid.

EXAMPLE I

Separation of cis- and trans-1,2-diamonocyclohexane

A solution of 1,2-diamonicyclohexanes (50.0 g; 0.44 mol) in methanol (200 ml) was added over a period of 2 min. to a stirred solution of NiCl$_2$.6H$_2$O (52.0 g; 0.22 mol) in methanol (500 ml). The initial light green solution turned dark blue-green after the diamine was added and a solid precipitate appeared in 20 min. The mixture was stirred for 3 hrs. then vacuum filtered to leave a yellow-green solid and a violet-blue filtrate. The solid was stirred in methanol (2×300 ml) for 2 hrs., vacuum filtered, and washed with methanol. The solid was dried, first in vacuo to remove traces of methanol then in a vacuum desiccator (P$_2$O$_5$) to yield 25.5 g of a yellow solid (the cis-1,2-diamonocyclohexane complex).

The violet-blue filtrate obtained above was acidified with 6N hydrochloric acid (60 ml) then the pH was adjusted to 4.2–4.5 with 20% aqueous sodium hydroxide. Violet crystals of the trans-1,2-diaminocyclohexane complex were deposited overnight. The crystals were filtered, washed with water and dried in a vacuum desiccator (P$_2$O$_5$) to give 29.0 g of a violet solid (trans-(d,1)-1,2-diaminocyclohexane complex).

EXAMPLE II

Cis-1,2-diaminocyclohexane

The yellow cis-1,2-diaminocyclohexanedichloronickel (II) (20 g) was added portionwise to a stirred 6N sulfuric acid (250 ml) over a period of 20 min. After 1 hr. the water was removed in vacuo to leave a viscous green oil. Absolute ethanol (160 ml) was added to the oil to produce a white solid. The solid was vacuum filtered, washed with absolute methanol and dried in a vacuum desiccator (P$_2$O$_5$) to give 20.0 g of a white solid (cis-1,2-diaminocyclohexane hydrosulfate).

The cis-1,2-diaminocyclohexane hydrosulfate (8.0 g; 0.33 mol) was added to 15% aqueous sodium hydroxide (60 ml) and continuously extracted with benzene for 8 hrs. The benzene was dried (K$_2$CO$_3$), filtered and evaporated in vacuo to leave 3.44 g (92%) of cis-1,2-diaminocycloxhexane as a colorless oil: ir (neat) 3362 (s), 3288 (s), 2942 (s), 2856 (s), 1592 (s), 1445 (s), and 846 (s) cm$^{-1}$; $^1$H-nmr (CDCl$_3$/TMS) δ 2.88 (2H, br), 1.50 (4H/6, br), 1.50 (4H, br), and 1.17 (4H, s); $^{13}$C-nmr (d-DMSO/TMS) δ 51.92, 30.74, and 21.93.

EXAMPLE III

Trans-(d,1)-1,2-diaminocyclohexane

This diamine was prepared in 76% yield by the same procedure used for the cis-diamine (Example II) except the violet trans(d,1)-1,2-diaminocyclohexanedichloronickel (II) was used. Trans-(d,1)-1,2-diaminocyclohexane had: ir (neat) 3355 (s), 3282 (s), 2942 (s), 1585 (s), 1445 (s), 953 (s), 893 (s), 866 (s), and 680 (s) cm$^{-1}$; $^1$H-nmr (CDCl$_3$/TMS) δ 2.45–2.10 (2H, br), 2.10–1.50 (4H, br), and 1.30 (4H, s).

EXAMPLE IV

General Procedure for the Separation/Optical Resolution of trans-1,2-diaminocyclohexane A 59.0 g portion of trans (d,1)-1,2-diaminocyclohexane was dissolved in 177 ml of water. To the stirred solution was added 22.2 g (147.7 mmol) of d-tartaric acid. To the solution was then added 42 ml (731 mmol) of glacial acetic acid, and the temperature of the reaction mixture increased to 60° C. A few crystals of (R,R)-(−)-trans-(d,1)-1,2-diaminocyclohexane were added to the hot reaction mixture, and it was allowed to cool to ambient temperature for a 4 hr. period. A crop of white crystals separated which was recovered by filtration and dried (11.2 g). The crystals were transferred to a liquid-liquid extractor, excess 20% NaOH solution was added to liberate trans-1,2-diaminocyclohexane from the tartrate salt, and the mixture was continuously extracted with benzene for 5 hrs. The benzene extract was evaporated under vacuum, leaving a solid crude product which was optically active (R,R)-(−)-trans-1,2-diaminocyclohexane. The crude product displayed [α]$_{589}$ $^{25}$ −36° (c 5.0, benzene) which corresponds to 86% optical purity. The weight of the crude product (4.48 g) corresponds to a 46% optical yield based on the amount of (R,R)-(−)-trans-(d,1)-1,2-diaminocyclohexane isomer contained in the starting amine and with correction of the product optical purity to 100%.

EXAMPLE V (1S, 2S), Trans-(d)-1,2-diaminocyclohexane

This optically active diamine was prepared in 72% yield by the method described in Example II for the conversion of cis-1,2-diaminocyclohexane hydrosulfate to cis-1,2-diaminocyclohexane except that trans-(d)-1,2-diaminocyclohexane ditartrate was used. The trans-(d)-1,2-diaminocyclohexane had: [α]$_{589}$ $^{25}$ = +33.7° (c=5; benzene).

EXAMPLE VI (1R,2R)-Trans-(1)-1,2-diaminocyclohexane

This optically active diamine was prepared in 70% yield by the method·described In Example V for the synthesis of the trans-(d)- isomer except that trans-(1)-1,2-diaminocyclohexane had: [α]$_{589}$$^{25}$ = −35.1° (c=5; benzene); lit. [α]$_{589}$$^{25}$ = 36.0°.

EXAMPLE VII

Cis-dichloro-cis-1,2-cyclohexanediammine platinum (II)

A mixture of cis-1,2-diaminocyclohexane (0.684 g; 6.0 mmol) and degassed water (5 ml; degassed by vacuum purging) was added to a stirred solution of potassium tetrachloroplatinate (II) (2.50 g; 6.0 mmol) in degassed water (25 ml) maintained under a blanket of nitrogen gas. The mixture was stirred for 18 hrs then vacuum filtered. The solid was washed with 1N hydrochloric acid, ethanol, and finally with diethyl ether. The air-dried material was a pale yellow solid (2.24 g; 98% yield). The solid was dissolved in dimethyl formamide, the mixture was filtered, and methanol was added to precipitate the cis-dichloro-cis-1,2-cyclohexanediammine platinum (II): ir (KBr) 3253 (s),.3118 (s), 2945 (s), 2862 (s), 1569 (s), 1445 (s), 1196 (s), 980 (s), and 762 cm$^-$(s).

The compound had very low solubility in water and methanol; it dissolved—50 mg/ml in DMF.

EXAMPLE VIII

Cis-dichloro-trans-(d,1)-1,2-cyclohexanediammine platinum (II)

This compound was prepared in 95% yield by the same procedure used for the synthesis of cis-dichloro-cis-1,2-cyclohexanediammine platinum (II) (Example VII) except that trans-(d,1)-1,2-cyclohexanediamine was used as starting material. The compound had: ir (KBr) 3274(s), 3193 (s), 2934 (s), 2866 (s), 1564 (s), 1160 (s), and 756 cm$^{-1}$ (s).

The compound had very low solubility in water and methanol; it dissolved in DMF—50 mg/ml.

Anal. Calcd for $C_6H_{14}N_2Cl_2Pt$: C, 18.96; H, 3.71; N, 7.37; Cl, 18.66. Found: C, 19.10; H, 3.71; N, 7.35; Cl, 18.71.

EXAMPLE IX

Cis-dichloro-trans-(1R,2R)-1,2-cyclohexanediammine platinum (II)

This compound was prepared by the same method used to synthesize the racemic (d,l)-mixture (Example VIII) except that trans-(1R,2R)-1,2-cyclohexanediamine was used as starting material.

EXAMPLE X

Cis-dichloro-trans-(1S,2S)-1,2-dichlorohexanediammine platinum (II)

This compound was prepared by the same method used to synthesize the racemic (d,l)-mixture (Example VIII) except that trans-(1S,2S)-1,2-cyclohexanediamine was used as starting material.

EXAMPLE XI (d,l)-Tetrachloro-trans-1,2-cyclohexanediammine platinum (IV)

Chlorine gas was bubbled at a rate of 2 bubbles second$^{-1}$ under the liquid surface of a stirred suspension of cis-dichloro-trans-(d,l)-1,2-cyclohexanediammine platinum (II) (2.10 g; 5.5 mmol) in 0.5N hydrochloric acid (40 ml) at 60° C. The temperature was raised to 100° C. as soon as the chlorine was introduced. The solid turned red-orange in color then to a bright yellow with a portion dissolving. Chlorine was bubbled into the mixture for 2.5 hrs then air was rapidly bubbled through the mixture to displace unreacted chlorine. The cooled reaction mixture was evaporated to dryness in vacuo, methanol (250 ml) was added to the yellow residue and the mixture was filtered. The filtrate was evaporated to dryness in vacuo to yield 2.14 g (87%) of a bright yellow solid: ir (KBr) 3228 (s), 3180 (s), 3090 (s), 2942 (s), 2863 (s), 1566 (s), 1450 (m), 1166 (s), 1060 (s), and 917 (m) cm$^{-1}$; $^1$H-nmr (d$^7$-DMF/TMS) 8.1–7.0 (br), 3.6 (br), 3.3 (s), 3.1 (br), 2.2 (br), 1.5 (br), and 0.7 (s); $^{13}$C-nmr (d$^7$-DMF/TMS) 63.96, 31.82, and 24.56.

The compound was soluble-ca. 6 mg/ml in water, 100 mg/mg in methanol, and 250 mg/ml in DMF.

EXAMPLE XII (1S,2S)-Tetrachloro-trans-1,2-cyclohexanediammine platinum (IV)

This compound was prepared by the procedure used (Example XI) to prepare the (d,l)-complex except: (1S,2S)-cis-dichloro-trans-1,2-cyclohexanediammine platinum (II) was used as starting material. The (1S,2S)-isomer had: $[\alpha]_{589}^{25} = 129.13$ (c=3.33, methanol). The compound was unexpectedly more soluble in water than the d,l-mixture, this pure isomer had a solubility in water of ca. 15 mg/ml.

Anal. Calcd for $C_6H_{14}N_2Cl_4Pt$: C, 15.98; H, 3.13; N, 6.21. Found: C, 16.01; H, 3.13; N, 6.12.

EXAMPLE XIII (1R,2R)-Tetrachloro-trans-1,2-cyclohexanediammine platinum (IV)

This compound was prepared by the procedure (Example XI) used to prepare the (d,l)-complex except: (1R,2R)-cis-dichloro-trans-1,2-cyclohexanediammine platinum (II) was used as starting material. The (1R,2R)-isomer had: $[\alpha]_{589}^{25} = +129.73$ (c=3.33, methanol). The compound was unexpectedly more soluble in water than the d,l-mixture, this pure isomer had a solubility in water of ca. 15 mg/ml.

Anal. Calcd for $C_6H_{14}N_2Cl_4Pt$: C, 15.98; H, 3.13; N, 31.44. Found: C, 16.05; H, 3.15; N, 6.20; Cl, 31.49.

EXAMPLE XIV

Tetrachloro-cis-1,2-cyclohexanediammine platinum (IV)

This compound was prepared by the same procedure (Example XI) used for the synthesis of the trans-(d,l) complex except that cis-dichloro-cis-1,2-cyclohexanediammine platinum (II) was used as starting material. Tetrachloro-cis-1,2-cyclohexanediammine platinum (II) had: ir (KBr) 3185 (s), 3090 (s), 2938 (s), 2865 (m), 1560 (s), 1451 (m), 1202 (s), 1131 (m), 976 (m), and 583 (m) cm$^{-1}$; $^{13}$C-nmr (d$^7$-DMF/TMS) δ 60.90, 26.30, and 21.72.

The compound was soluble —10 mg/ml in water, ~50 mg/ml in methanol, ~200 mg/ml methanol-acetone (1:1), and ~250 mg/ml in DMF.

Anal. Calcd for $C_6H_{14}N_2Cl_4Pt$: C, 15.98; H, 3.13; N, 6.21; Cl, 31.44. Found: C, 16.25; H, 3.20; N, 6.09; Cl, 31.17.

EXAMPLE XV

Infrared Spectroscopy as a Method to Determine the Amount of Pt (II) Present in Samples of Pt (IV)

A very strong rocking absorption, pNH$_2$, at 756 cm$^{-1}$ in the cis-dichloro-trans-1,2-cyclohexanediammine platinum (II) was absent in the spectrum of the corresponding platinum (IV) compound. Application of the Beer-Lambert laws showed that there was less than 1% of platinum (II) in the sample of (d,l)-tetrachloro-trans-1,2-cyclohexanediammine platinum (IV). Similar analyses of the spectra of the 1S,2S- and 1R,2R-isomers showed comparable purity.

The strong rocking triplet absorption, pNH$_2$, centered at 761 cm$^{-1}$ in the cis-dichloro-cis-1,2-cyclohexanediammine platinum (II) was absent in the corresponding Pt (IV) compound. Again, less than 1% of Pt (II) was present in the sample of tetrachloro-cis-1,2-cyclohexanediammine platinum (IV).

EXAMPLE XVI

High Pressure Liquid Chromatography

The HPLC studies were carried out using a Spectra Physics SP8000 equipped with a Varian Varichrome variable wavelength detector. The injection volumes were 10 µl, injection concentrations were 1–2 mg/ml, flow rates were 1–2 ml/min. The UV detector was set to monitor 254 nm. The column, a Dupont Zorbax C-8 reversed phase column (25 cm×4.6 mm), was eluted with 0.0075 aqueous phosphate buffer.

All compounds injected were shown to be greater than 99% pure by the above system. Separation of the Pt (II) and Pt (IV) compounds could not be demonstrated with either system. The extinction coefficient of Pt (II) was much lower than the extinction coefficient of Pt (IV), (0.1ϵ Pt (IV)~ϵPt (II).

We claim:

1. A process of preparing pharmacologically pure tetrachloro-1,2-diaminocyclohexane platinum (IV) which comprises the sequential steps of:

(a) reacting 1,2-diaminocyclohexane with alkali metal chlorplatinate in degassed water in an inert atmosphere and isolating the thus formed 1,2-dichloro-1,2-diaminocyclohexane platinum (II) therefrom, (b) suspending dichloro-1,2-diaminocyclohexane platinum (II) in aqueous hydrochloric acid, passing chlorine gas therethru, removing unreacted chlorine from the reaction mixture and isolating the tetrachloro-1,2-diaminoxyclohexane platinum (IV) therefrom.

2. A process of preparing tetrachlorine-cis-1,2-cyclohexanediamine platinum (IV) which comprises carrying out the process of claim 1 starting with 1,2-cis-diaminocyclohexane.

3. A process for the preparation of (d,1)-1-tetrachloro-trans-1,2-cyclohexanediamine platinum (IV) which comprises carrying out the process of claim 1 starting with trans-(d,1)-1,2-cyclohexanediamine.

4. A process of preparing (1S,2S)-tetrachloro-trans-1,2-cyclohexanediamine platinum (IV) which comprises carrying out the process of claim 1 starting with trans-(1R,2R)-1,2-cyclohexanediamine.

5. A process of preparing (1S,2S)-tetrachloro-trans-1,2-cyclohexanediamine platinum (IV) which comprises carrying out the process of claim 1 starting with trans-(1S,2S)-1,2-cyclohexanediamine.

* * * * *